(12) United States Patent
Yao et al.

(10) Patent No.: US 10,738,077 B1
(45) Date of Patent: Aug. 11, 2020

(54) HYDROXYTYROSOL URSODEOXYCHOLIC ACID ESTER WITH ANTIOXIDANT ACTIVITY AND A METHOD OF PREPARING THE SAME

(71) Applicants: Wenbo Yao, Xi'an (CN); Guaiping Qiao, Xi'an (CN); Juan Li, Xi'an (CN); Nan Hui, Xi'an (CN); Qiao Zeng, Xi'an (CN); Han Li, Xi'an (CN); Bin Tian, Xi'an (CN); Yongbo Wang, Xi'an (CN); Dan Yang, Xi'an (CN); Jingwen Xu, Xi'an (CN); Liang Qi, Xi'an (CN); Yanjun Li, Xi'an (CN); Chengyuan Liang, Xi'an (CN)

(72) Inventors: Wenbo Yao, Xi'an (CN); Guaiping Qiao, Xi'an (CN); Juan Li, Xi'an (CN); Nan Hui, Xi'an (CN); Qiao Zeng, Xi'an (CN); Han Li, Xi'an (CN); Bin Tian, Xi'an (CN); Yongbo Wang, Xi'an (CN); Dan Yang, Xi'an (CN); Jingwen Xu, Xi'an (CN); Liang Qi, Xi'an (CN); Yanjun Li, Xi'an (CN); Chengyuan Liang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/845,038

(22) Filed: Apr. 9, 2020

(51) Int. Cl.
*C07J 9/00* (2006.01)
*C07C 29/10* (2006.01)
*A61K 47/28* (2006.01)

(52) U.S. Cl.
CPC ............... *C07J 9/005* (2013.01); *C07C 29/10* (2013.01); *A61K 47/28* (2013.01)

(58) Field of Classification Search
CPC ........... C07J 9/005; A61K 47/28; C07C 29/10
See application file for complete search history.

(56) References Cited

U.S. PATENT DOCUMENTS

2020/0101030 A1\* 4/2020 Casey, Jr. ............ A61K 31/164

\* cited by examiner

*Primary Examiner* — Jafar F Parsa

(57) ABSTRACT

A compound having the formula (I):

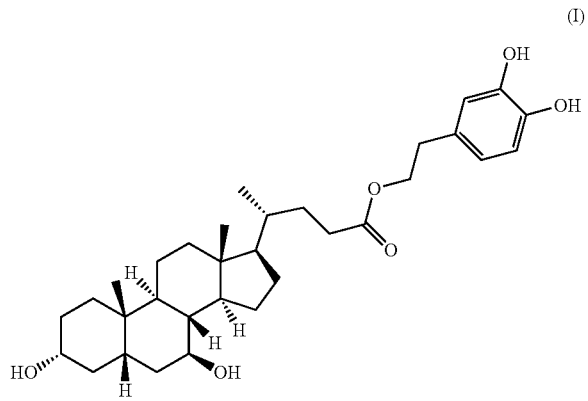

is disclosed. A method of preparing the compound of formula (I) is also disclosed.

15 Claims, 1 Drawing Sheet

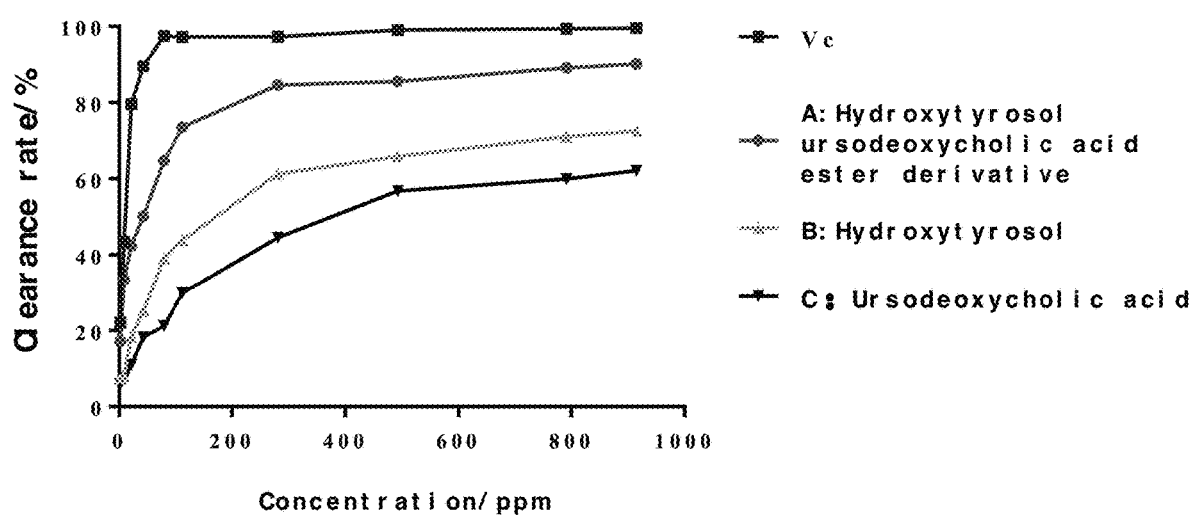

HYDROXYTYROSOL URSODEOXYCHOLIC ACID ESTER WITH ANTIOXIDANT ACTIVITY AND A METHOD OF PREPARING THE SAME

FIELD OF THE INVENTION

The present invention relates to food chemistry, specifically, a hydroxytyrosol ursodeoxycholic acid ester and a method of preparing the same.

BACKGROUND OF THE INVENTION

Worldwide health survey shows that cardiovascular disease, cancer and diabetes have become the three major diseases that threaten human life. Studies have shown that oxidative stress is the main cause of cardiovascular disease, cancer and Alzheimer's disease. Oxidative stress means that when the body is subjected to a variety of harmful stimuli, the body produces too many highly active molecular free radicals and accumulates a large number of free radicals, resulting in the imbalance between oxidation system and antioxidant system. Antioxidants and antioxidant functional foods can effectively inhibit the oxidation of free radicals, thus effectively preventing the occurrence of various diseases related to free radicals. However, traditional synthetic antioxidants, such as tert-butyl p-hydroxyanisole (BHA) and dibutyl hydroxytoluene (BHT), may be potentially toxic and harmful to human health. Therefore, there is a need for new potent and safe antioxidants.

Hydroxytyrosol is a kind of natural polyphenols (compound of formula II), which has a variety of biological and pharmacological activities and can be derived from olive oil and wastewater from olive oil processing. It is used as a food additive.

Ursodeoxycholic acid (compound of formula III) is a chemical for the separation of natural bile acid from bear bile. It is a diastereomer of chenodeoxycholic acid. Its stone-dissolving effect and curative effect are similar to those of chenodeoxycholic acid, but the course of treatment is short and the dose is small. It can be used to treat cholesterol stones, primary biliary cirrhosis, chronic hepatitis, bile reflux gastritis and prevent acute rejection and reaction of liver transplantation.

In the present invention, the ursodeoxycholic acid is modified by hydroxytyrosol to obtain a hydroxytyrosol ursodeoxycholic acid ester. This ester has excellent antioxidant activity and has high medical research and application value in the field of antioxidant health products.

SUMMARY OF THE INVENTION

In one embodiment, the present invention provides a compound having the following formula (I):

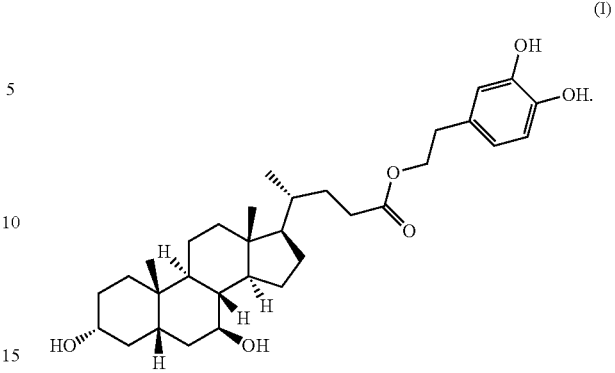

In another embodiment, the present invention provides a method of preparing the compound of formula (I). The method includes: reacting the compound of formula (II) with the compound of formula (III) to obtain the compound of formula (I):

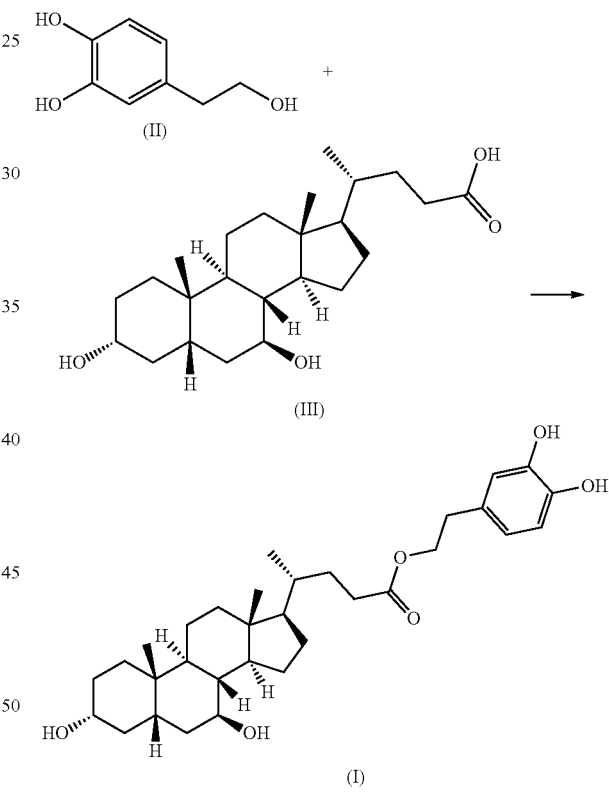

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; heating the reaction mixture at 60-90° C. for 4-8 hours; concentrating the reaction mixture to give a crude product; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is acetonitrile.

In another embodiment, the molar ratio of the compound of formula (II) and the compound of formula (III) is 1:1.1.

In another embodiment, the reaction mixture is heated at 80° C.

In another embodiment, the reaction mixture is heated for 7 hours.

In another embodiment, the eluent is petroleum ether: ethyl acetate=3:10.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 30-60° C. for 5-12 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][$BF_4$]).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 25° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the scavenging activity of the compound of formula (I) and control solutions at different concentrations.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of (R)-3,4-dihydroxyphenethyl 4-((3R, 5S,7S,8R,9R,10S,13R,14R,17R)-3,7-dihydroxy-8, 10,13-trimethylhexadecahydro-1H-cyclopenta[a] phenanthren-17-yl)pentanoate (Compound of Formula I)

In a 250 mL three-necked flask, 77.0 mg (0.50 mmol) of hydroxytyrosol and 95.8 mg (0.50 mmol) EDC (1-ethyl-3-(3-dimethylaminopropyl)carbodiimide) were dissolved in 50 mL of acetonitrile under nitrogen atmosphere. 215.9 mg (0.55 mmol) of ursodeoxycholic acid was dissolved in 90 mL of acetonitrile, and slowly added dropwise to the reaction mixture by a separatory funnel. After the completion of the dropwise addition, the temperature was raised to 80° C., and the reaction was carried out for 7 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography with petroleum ether: ethyl acetate=3:10 as eluent. The eluent was concentrated under reduced pressure and dried to obtain the title compound, 210.9 mg, a yield of 79.85%.

$^1$H-NMR (400 MHz, DMSO-$d^6$) δ (ppm): 6.86 (1H, s), 6.66 (1H, s), 6.65 (1H, s), 5.08 (2H, s), 4.21 (2H, t), 3.42 (2H, d) 3.13 (2H, s), 2.90 (2H, t), 2.15 (2H, t), 1.81 (2H, t), 1.60~1.31 (16H, t), 1.31~1.06 (6H, s), 1.06 (6H, s), 1.00 (3H, d); $^{13}$C-NMR (400 MHz, DMSO-$d_6$) δ ppm): 175.3, 145.3, 143.7, 130.6, 119.8, 116.7, 70.2, 69.9, 63.0, 56.3, 40.4, 39.2, 38.1, 35.2, 31.2, 28.5, 23.7, 18.7, 12.4.

Example 2

Preparation of (R)-3,4-dihydroxyphenethyl 4-((3R, 5S,7S,8R,9R,10S,13R,14R,17R)-3,7-dihydroxy-8, 10,13-trimethylhexadecahydro-1H-cyclopenta[a] phenanthren-17-yl)pentanoate In a 250 mL three-necked flask, 77.0 mg (0.50 mmol) of hydroxytyrosol and 95.8 mg (0.50 mmol) EDC were dissolved in 50 mL of toluene under nitrogen atmosphere. 215.9 mg (0.55 mmol) of ursodeoxycholic acid was dissolved in 90 mL of toluene, and slowly added dropwise to the reaction mixture by a separatory funnel. After the completion of the dropwise addition, the temperature was raised to 60° C., and the reaction was carried out for 8 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography with petroleum ether:ethyl acetate=3:10 as eluent. The eluent was concentrated under reduced pressure and dried to obtain the title compound, 207.5 mg, a yield of 78.55%.

Example 3

Preparation of (R)-3,4-dihydroxyphenethyl 4-((3R, 5S,7S,8R,9R,10S,13R,14R,17R)-3,7-dihydroxy-8, 10,13-trimethylhexadecahydro-1H-cyclopenta[a] phenanthren-17-yl)pentanoate In a 250 mL three-necked flask, 77.0 mg (0.50 mmol) of hydroxytyrosol and 95.8 mg (0.50 mmol) EDC were dissolved in 50 mL of tetrahydrofuran under nitrogen atmosphere. 215.9 mg (0.55 mmol) of ursodeoxycholic acid was dissolved in 90 mL of tetrahydrofuran, and slowly added dropwise to the reaction mixture by a separatory funnel. After the completion of the dropwise addition, the temperature was raised to 80° C., and the reaction was carried out for 4 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography with petroleum ether:ethyl acetate=3:10 as eluent. The eluent was concentrated under reduced pressure and dried to obtain the title compound, 191.3 mg, a yield of 72.43%.

Example 4

Preparation of (R)-3,4-dihydroxyphenethyl 4-((3R,5S,7S,8R,9R,10S,13R,14R,17R)-3,7-dihydroxy-8,10,13-trimethylhexadecahydro-1H-cyclopenta[a]phenanthren-17-yl)pentanoate In a 250 mL three-necked flask, 77.0 mg (0.50 mmol) of hydroxytyrosol and 95.8 mg (0.50 mmol) EDC were dissolved in 50 mL of toluene, and nitrogen gas was added thereto. 215.9 mg (0.55 mmol) of ursodeoxycholic acid was dissolved in 90 mL of toluene, and slowly added dropwise to the reaction liquid by a separatory funnel. After the completion of the dropwise addition, the temperature was raised to 75° C., and the reaction was carried out for 5 hours. Thin layer chromatography was used to track the reaction to completion, heating was stopped, and the protective device was removed. The concentrated solution was washed in water, extracted with ethyl acetate, dried and concentrated, and the crude hydroxytyrosol ursodeoxycholic acid ester derivative was obtained. The crude product was further adsorbed and purified by silica gel column chromatography, petroleum ether:ethyl acetate=3:10 as eluent, and the eluent was concentrated under reduced pressure and dried to obtain hydroxytyrosol ursodeoxycholic acid ester derivative. The acid ester derivative was 181.8 mg, and the total yield was 68.83%.

Example 5

Preparation of Compound (R)-3,4-dihydroxyphenethyl 4-((3R,5S,7S,8R,9R,10S,13R,14R,17R)-3,7-dihydroxy-8,10,13-trimethylhexadecahydro-1H-cyclopenta[a]phenanthren-17-yl)pentanoate In a 250 mL three-necked flask, 77.0 mg (0.50 mmol) of hydroxytyrosol and 95.8 mg (0.50 mmol) EDC were dissolved in 50 mL of acetonitrile under nitrogen atmosphere. 215.9 mg (0.55 mmol) of ursodeoxycholic acid was dissolved in 90 mL of acetonitrile, and slowly added dropwise to the reaction mixture by a separatory funnel. After the completion of the dropwise addition, the temperature was raised to 70° C., and the reaction was carried out for 6 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography with petroleum ether:ethyl acetate=1:6 as eluent. The eluent was concentrated under reduced pressure and dried to obtain the title compound, 196.9 mg, a yield of 74.53%.

Example 6

Preparation of (R)-3,4-dihydroxyphenethyl 4-((3R,5S,7S,8R,9R,10S,13R,14R,17R)-3,7-dihydroxy-8,10,13-trimethylhexadecahydro-1H-cyclopenta[a]phenanthren-17-yl)pentanoate In a 250 mL three-necked flask, 77.0 mg (0.50 mmol) of hydroxytyrosol and 95.8 mg (0.50 mmol) EDC were dissolved in 50 mL of tetrahydrofuran under nitrogen atmosphere. 215.9 mg (0.55 mmol) of ursodeoxycholic acid was dissolved in 90 mL of tetrahydrofuran, and slowly added dropwise to the reaction mixture by a separatory funnel. After the completion of the dropwise addition, the temperature was raised to 50° C., and the reaction was carried out for 7 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography with petroleum ether:ethyl acetate=1:6 as eluent. The eluent was concentrated under reduced pressure and dried to obtain the title compound, 169.5 mg, a yield of 64.18%.

Example 7

Preparation of Compound (R)-3,4-dihydroxyphenethyl 4-((3R,5S,7S,8R,9R,10S,13R,14R,17R)-3,7-dihydroxy-8,10,13-trimethylhexadecahydro-1H-cyclopenta[a]phenanthren-17-yl)pentanoate In a 100 mL three-necked flask, 77.0 mg (0.50 mmol) of hydroxytyrosol, 215.9 mg (0.55 mmol) of ursodeoxycholic acid and 9.2 mg (0.005 mmol) silicomolybdic acid were dissolved in 50 mL of 1-Ethyl-3-methylimidazolium hexafluorophosphate, and nitrogen gas was added thereto. After full dissolution, the temperature was raised to 30° C. and the reaction was carried out for 10 hours. Thin layer chromatography was used to track the reaction to completion, heating was stopped, and the protective device was removed. The reaction mixture system was allowed to separate into layers to give a crude hydroxytyrosol ursodeoxycholic acid ester derivative. The crude product was recrystallized with 50 mL methanol and dried to obtain hydroxytyrosol ursodeoxycholic acid ester derivative. The acid ester derivative was 233.0 mg, and the total yield was 88.21%.

Example 8

Preparation of (R)-3,4-dihydroxyphenethyl 4-((3R,5S,7S,8R,9R,10S,13R,14R,17R)-3,7-dihydroxy-8,10,13-trimethylhexadecahydro-1H-cyclopenta[a]phenanthren-17-yl)pentanoate In a 100 mL three-necked flask, 77.0 mg (0.50 mmol) of hydroxytyrosol, 215.9 mg (0.55 mmol) of ursodeoxycholic acid and 9.2 mg (0.005 mmol) silicomolybdic acid were dissolved in 50 mL of 1-Ethyl-3-methylimidazolium hexafluorophosphate, and nitrogen gas was added thereto. After full dissolution, the temperature was raised to 60° C. and the reaction was carried out for 5 hours. Thin layer chromatography was used to track the reaction to completion, heating was stopped, and the protective device was removed. The reaction mixture system was allowed to separate into layers to give a crude hydroxytyrosol ursodeoxycholic acid ester derivative. The crude product was recrystallized with 50 mL methanol and dried to obtain hydroxytyrosol ursodeoxycholic acid ester derivative. The acid ester derivative was 215.5 mg, and the total yield was 81.58%.

Example 9

The antioxidant activity of the hydroxytyrosol ursodeoxycholic acid ester derivative measured by a DPPH radical scavenging activity assay 2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in toluene to prepare a 0.2 mmoL/L DPPH solution, stored at 0° C. in dark.

Preparation of test solution: Vc (vitamin C, positive control), hydroxytyrosol ursodeoxycholic acid ester derivative (sample), hydroxytyrosol (control) and ursodeoxycholic acid (control). The sample solution was subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 1).

TABLE 1

Dilution gradient of the test solution

| Number | Test solution | Concentration gradient/ppm |
|---|---|---|
| Vc | Vc | 1.76, 8.80, 21.12, 42.24, 79.20, 112.64, 281.60, 492.80, 792.00, 915.20 |
| A | Hydroxytyrosol ursodeoxycholic acid ester derivative | 1.76, 8.80, 21.12, 42.24, 79.20, 112.64, 281.60, 492.80, 792.00, 915.20 |
| B | Hydroxytyrosol | 1.76, 8.80, 21.12, 42.24, 79.20, 112.64, 281.60, 492.80, 792.00, 915.20 |
| C | Ursodeoxycholic acid | 1.76, 8.80, 21.12, 42.24, 79.20, 112.64, 281.60, 492.80, 792.00, 915.20 |

Specific Steps:

Sample liquid absorbance measurement: Take 2 mL of sample solution (Table 1: Vc, A, B, C), add 2 mL of DPPH solution with concentration of $2 \times 10^{-4}$ moL/L, mix and react in the dark at room temperature for 30 min, adjust to zero with toluene, and measure at 517 nm. The absorbance Ai was simultaneously measured for the absorbance Aj of 2 mL of toluene mixed with 2 mL of the sample solution and the absorbance Ao of 2 mL of DPPH solution mixed with 2 mL of toluene (The experimental results are shown in Table 2).

TABLE 2 absorbance test results of each test solution

| Sample | Absorbance | \multicolumn{10}{c}{Concentration/ppm} |
|---|---|---|---|---|---|---|---|---|---|---|---|

| Sample | Absorbance | 1.76 | 8.80 | 21.12 | 42.24 | 79.20 | 112.64 | 281.60 | 492.80 | 792.00 | 915.20 |
|---|---|---|---|---|---|---|---|---|---|---|---|
| Vc | Ai | 0.726 | 0.539 | 0.222 | 0.142 | 0.091 | 0.080 | 0.085 | 0.070 | 0.074 | 0.063 |
|  | Aj | 0.068 | 0.061 | 0.050 | 0.054 | 0.069 | 0.057 | 0.062 | 0.062 | 0.066 | 0.059 |
|  | Ao |  |  |  |  |  | 0.846 |  |  |  |  |
| A | Ai | 0.740 | 0.602 | 0.541 | 0.466 | 0.348 | 0.354 | 0.186 | 0.167 | 0.147 | 0.133 |
|  | Aj | 0.052 | 0.049 | 0.061 | 0.052 | 0.055 | 0.061 | 0.058 | 0.047 | 0.057 | 0.051 |
|  | Ao |  |  |  |  |  | 0.832 |  |  |  |  |
| B | Ai | 0.918 | 0.904 | 0.810 | 0.739 | 0.630 | 0.580 | 0.403 | 0.365 | 0.305 | 0.293 |
|  | Aj | 0.053 | 0.046 | 0.047 | 0.039 | 0.060 | 0.055 | 0.041 | 0.046 | 0.034 | 0.036 |
|  | Ao |  |  |  |  |  | 0.935 |  |  |  |  |
| C | Ai | 0.890 | 0.880 | 0.925 | 0.779 | 0.755 | 0.680 | 0.542 | 0.438 | 0.405 | 0.375 |
|  | Aj | 0.048 | 0.052 | 0.049 | 0.048 | 0.051 | 0.053 | 0.046 | 0.052 | 0.047 | 0.036 |
|  | Ao |  |  |  |  |  | 0.895 |  |  |  |  |

Clearance calculation: clearance rate (%)=[1−(Ai−Aj)/Ao]*100%

TABLE 3

DPPH clearance rate experiment results

| Concentration/ppm | \multicolumn{4}{c}{Clearance rate/% (n = 3)} |
|---|---|---|---|---|

| Concentration/ppm | Vc | A | B | C |
|---|---|---|---|---|
| 1.76 | 22.16 | 17.23 | 7.42 | 5.85 |
| 8.80 | 43.47 | 33.56 | 8.16 | 7.45 |
| 21.12 | 79.63 | 42.35 | 18.43 | 11.02 |
| 42.24 | 89.55 | 50.23 | 25.10 | 18.22 |
| 79.20 | 97.42 | 64.74 | 38.99 | 21.24 |
| 112.64 | 97.23 | 73.56 | 43.87 | 29.89 |
| 281.60 | 97.29 | 84.63 | 61.25 | 44.51 |
| 492.80 | 99.01 | 85.52 | 65.88 | 56.82 |
| 792.00 | 99.35 | 89.13 | 71.03 | 59.94 |
| 915.20 | 99.52 | 90.11 | 72.55 | 62.13 |

According to the experimental results of FIG. 1 and Table 1-3, the antioxidant activity of hydroxytyrosol ursodeoxycholic acid ester derivative (A) showed a concentration-dependent relationship, and the scavenging ability of compound A to DPPH radical increased with the increase of concentration. In the determined concentration range, the highest scavenging rate of DPPH radical was 90.11%. At the same time, compared with the positive control Vc group, the scavenging ability of hydroxytyrosol ursodeoxycholic acid ester derivative (A) was weaker. However, it still has obvious clearance ability. Compared with the control group treated with hydroxytyrol (B) and ursodeoxycholic acid (C) alone, the scavenging ability of (A), a derivative of hydroxycaseol ursodeoxycholic acid, to scavenge DPPH free radicals was mostly better at the same concentration. The antioxidant activity at higher concentration was much higher than that of hydroxytyrosol (B) control group and ursodeoxycholic acid (C) control group. The above experimental results prove that the compound has excellent antioxidant activity and a good application prospect.

What is claimed is:

1. A compound having the following formula (I):

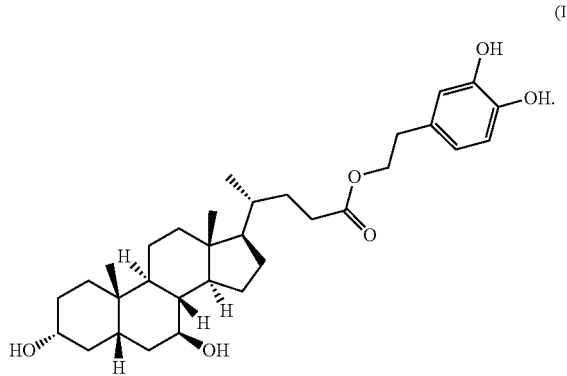 [SMILES: C[C@H](CCC(=O)OCCc1ccc(O)c(O)c1)[C@H]1CC[C@H]2[C@@H]3[C@@H](O)C[C@@H]4C[C@H](O)CC[C@]4(C)[C@H]3CC[C@]12C]

2. A method of preparing the compound of formula (I) of claim 1, comprising:
reacting the compound of formula (II) with the compound of formula (III) to obtain the compound of formula (I):

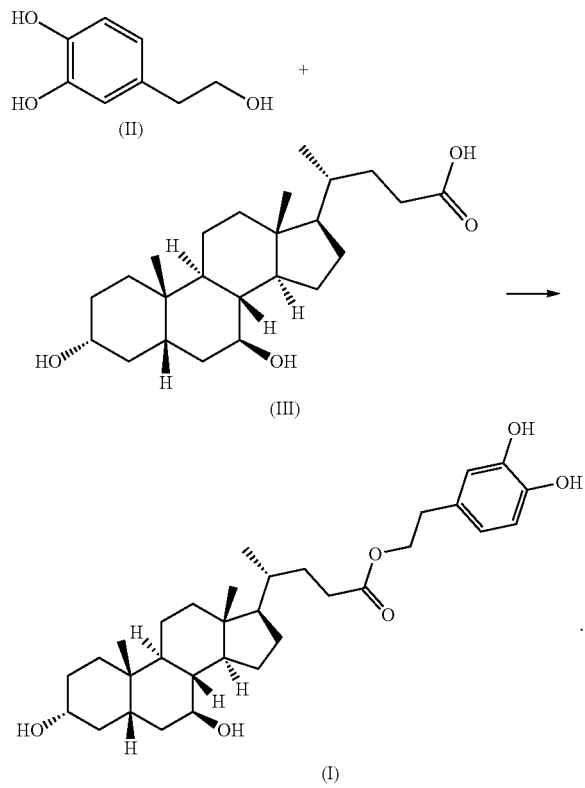

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of EDC to obtain a reaction mixture;
heating the reaction mixture at 60-90° C. for 4-8 hours;
concentrating the reaction mixture to give a crude product; and
purifying the crude product on a silica gel fresh chromatography column with petroleum ether and ethyl acetate as an eluent to obtain the compound of formula (I).

4. The method of claim 3, wherein the organic solvent is toluene, tetrahydrofuran or acetonitrile.

5. The method of claim 4, wherein the organic solvent is acetonitrile.

6. The method of claim 3, wherein the molar ratio of the compound of formula (II) and the compound of formula (III) is 1:1.1.

7. The method of claim 3, wherein the reaction mixture is heated at 80° C.

8. The method of claim 3, wherein the reaction mixture is heated for 7 hours.

9. The method of claim 3, wherein the eluent is petroleum ether:ethyl acetate=3:10.

10. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 30-60° C. for 5-12 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-butyl-3-methylimidazolium tetrafluoroborate ([BMIM][BF$_4$]).

12. The method of claim 10, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 10, wherein the reaction mixture is heated at 25° C.

15. The method of claim 10, wherein the reaction mixture is heated for 8 hours.

* * * * *